United States Patent [19]

Clemens

[11] Patent Number: 6,026,817
[45] Date of Patent: *Feb. 22, 2000

[54] METHOD OF TREATING THE SYNDROME OF CORONARY HEART DISEASE RISK FACTORS IN HUMANS

[76] Inventor: Anton H. Clemens, 5854 Schumann Dr., Madison, Wis. 53711

[*] Notice: This patent is subject to a terminal disclaimer.

[21] Appl. No.: 09/058,767

[22] Filed: Apr. 11, 1998

Related U.S. Application Data

[63] Continuation-in-part of application No. 08/937,996, Sep. 26, 1997, Pat. No. 5,878,750, which is a continuation-in-part of application No. 08/749,333, Nov. 14, 1996, Pat. No. 5,727,570.

[51] Int. Cl.[7] .................................................. A61B 19/00
[52] U.S. Cl. ............................................. 128/898; 604/49
[58] Field of Search ....................... 128/898; 604/890.1, 604/891.1, 892.1, 49; 424/473, 486, 467, 482, 485–88; 514/467, 120, 161, 195, 201, 202, 203, 204, 205–208

[56] References Cited

PUBLICATIONS

Sohel et al. "Influence of Adrenergic Blockers and Antilipemic Agents on Pharmacodynamic Actions of Morphine in Carbon Tetrachloride–Treated Rats." Toxicol Appl Pharmacol 27(3):477–483, Mar. 1974.

Stern et al. "Lack of Awareness and Treatment of yperlipidemia in Type II Diabetes in a Community Survey." JAMA 262(3):360–4, Jul. 1989.

*Primary Examiner*—Mickey Yu
*Assistant Examiner*—Kelly O'Hara
*Attorney, Agent, or Firm*—John H. Engelmann

[57] ABSTRACT

A method of treatment of humans suffering from the Coronary Heart Disease Risk Factor (CHDRF) Syndrome which comprises the steps of 1) administering, by a pharmaceutically effective mode, a priming dose of drug composition selected from the group consisting of opiate antagonists, and drugs which substantially equally reduce the amounts of catecholamines bound to catecholamine binding sites for a period of about one to four weeks, and 2) administering a maintenance dose of said selected drug, is disclosed.

22 Claims, No Drawings

METHOD OF TREATING THE SYNDROME OF CORONARY HEART DISEASE RISK FACTORS IN HUMANS

This is a continuation-in-part of U.S. Pat. No. 5,878,750 which is a continuation-in-part of U.S. Pat. No. 5,727,570.

BACKGROUND OF THE INVENTION

Coronary heart disease is one of the major causes of death in the industrialized world. The major coronary heart disease (CHD) risk factors are hyperlipidemia, type 2 diabetes / impaired glucose tolerance (IGT), obesity and essential hypertension, that is, a form of hypertension occurring without discoverable organic cause. The coronary heart disease risk factor syndrome (CHDRF syndrome) may be defined as a group of diseases, that is, hyperlidemia, Type 2 diabetes / impaired glucose tolerance (IGT), obesity and essential hypertension which individually, and together are among the major risk factors in coronary heart disease. The disease states which make up the syndrome of the coronary heart disease risk factors (CHDRF syndrome) are all interrelated. However, the exact interrelationship between the disease states making up the syndrome is not frilly understood. There are a wide variety of chemical and physical abnormalities associated with the CHDRF syndrome. These abnormalities include elevation in fasting blood glucose, elevation of HgbAlc, elevation of C-peptide, elevation of fasting total cholesterol, elevation of fasting LDL-cholesterol, decrease in fasting HDL-cholesterol, a high LDL/HDL ratio, elevation of fasting triglycerides, elevation of fasting free fatty acid concentration, elevation in body weight, elevation of systolic blood pressure, and elevation of diastolic blood pressure.

Although the entire CHDRFS is interrelated, individual patients may not present all the symptoms associated with the syndrome. Accordingly, in some patients the lipid metabolism problems may predominate, while in others, the glucose metabolism problems play a more major role. The factors, which lead one aspect of the syndrome to predominate over another, are not well understood. However, it is clear that each portion of the syndrome, or combination of portions of the syndrome, represents a risk factor in coronary heart disease.

Hyperlipidemia, also called dislipidemia, is characterized by elevated levels of total and low density lipoprotein cholesterol (LDL cholesterol), elevated levels of triglycerides and low levels of high density lipoprotein cholesterol (HDL cholesterol), as well as elevated levels of free fatty acids. State-of-the-art therapeutic regimens have failed to treat and correct the entire complex of hyperlipidemia with a single pharmaceutical agent. Drugs such as clofibrate/gemfibrozil lower triglycerides, by some unknown mechanism, but have no effect of the free fatty acid level, and no effect upon the total cholesterol level. However, the drugs may shift the proportion of cholesterol found in the form of low and high density lipoprotein cholesterol. In patients suffering from an elevated level of low density lipoprotein cholesterol, the drugs may actually further increase the level of low density lipoprotein cholesterol. Drugs like lovastatin, on the other hand, lower the level of both total and low density lipoprotein cholesterol, while slightly increasing the level of high density lipoprotein cholesterol. However, these drugs have no effect on free fatty acids and little or no effect on triglyceride levels.

Lipid metabolism is rather complex. While it is clear that hyperlipidemia is associated with the development of coronary heart disease, there is no clear understanding of the pathogenic causes and pathways leading up to the manifestation of the various lipid disorders, nor is there any agreement as to the relative roles of lipid ingestion versus endogenous lipogenesis in the etiology of lipid abnormnalities. Insulin resistance has, traditionally, been considered a state in which a normal amount of insulin produces a subnormal biological response, as is the case in non-insulin-dependent diabetics and/or in pre-diabetic subjects affected by glucose intolerance or impaired glucose tolerance. These subjects require (and endogenously produce) higher than normal levels of insulin to compensate for their insulin resistance to normalize their blood glucose levels. As a consequence, the traditional definition of insulin resistance was expressed in the insulin/glucose ratio (I/G). It has only been recently that other biological functions of insulin have become the focus of more intense scientific interest, e.g. the role of insulin in endogenous lipogenesis. Although an interaction between obesity and insulin resistance has been established, the cause and effect relationship between these syndromes is still hotly debated in the scientific community: which comes first, insulin resistance or obesity or hyperlipidemia. Whatever the exact cause(s) of hyperlipidemia may be, current therapeutic modalities of lowering one or the other lipid fraction are not capable of correcting the entire hyperlipidemic complex at or close to its original cause.

Type 2 diabetes, also known as maturity-onset diabetes, as opposed to type 1 diabetes, or juvenile diabetes, is characterized by inadequate endogenous insulin concentrations, although, in absolute terms, the insulin concentrations in type 2 diabetics may, in fact, be higher than in the normal population. A possible explanation for this apparent discrepancy may lie in the fact that type 2 diabetics, as well as subjects with impaired glucose tolerance (IGT), typically require more insulin to control their blood sugar level. The requirement for more insulin may be caused, in part, by a resistance to the action of insulin on the control of glucose. It is important to note that resistance to the action of insulin on the control of glucose may not carry over to the action of insulin on lipogenesis. Even though the patient is resistant to the action of insulin in controlling glucose, the response of lipid metabolism to insulin may remain. Thus, when the level of insulin rises due to the patient's insulin resistance, the elevation in insulin concentration may cause an increase in lipogenesis which, in turn, may lead to hyperlipidemia Current pharmaceutical modalities to treat the symptoms of type 2 diabetes have generally no beneficial effect on hyperlipidemia; some of the widely used medicines to treat type 2 diabetes, e.g. the sulfonylureas, tend to increase hyperlipidemia. Impaired glucose tolerance can be considered a precursor of type 2 diabetes. IGT is a phase at which the abnormal elevation of insulin concentration is still able to maintain a normal fasting blood sugar level. Over time, the insulin releasing beta-cells appear to lose their ability to produce enough insulin, and the subject slowly 'decompensates' to the state of 'overt' diabetes.

Obesity is now being recognized as a disease of major proportions and severe economic consequences, and not merely a physical or cosmetic inconvenience. Obesity is second only to cigarette smoking as a preventable cause of premature death, and its complications add $ 100 billion to the U.S. health care cost. Obesity can not be treated effectively by willpower alone, and pharmaceutical drugs, currently available are either in-effective long-term, or carry the risk of potentially fatal side-effects, like pulmonary hypertension or heart defects in connection with dexfenfluramin or fenfluramine. Six out of ten, or approximately 130 million people, in the United States are overweight, close to 90 million are obese and 22 million are morbidly obese.

The definition of obesity and normal weight is somewhat arbitrary. The disease of being overweight or obese is characterized by excess body fat, that is, the body contains a level of fat beyond that considered normal. Often, body weight in relationship to height and build is used as a surrogate measure. A weight of 20% over that in the standard height weight tables is considered obese. Normal weight has several definitions. The body mass index (BMI) is commonly used in defining normal weight. The BMI is calculated by dividing a person's weight in kilograms by the square of height in meters ($kg/m^2$) or ($lbs.\times 705/inches^2$). A BMI of 25 is considered normal, a BMI of 25–27 is considered overweight, a BMI 27–40 is considered obese, and a BMI>40 is considered morbid. A therapeutic intervention is considered effective if it produces a weight reduction of >10% or a reduction by >5% if 'co-morbid' factors are also improved, e.g. hyperlipidemia or diabetes.

Hyperlidemia, also known as disilpidemia, is a group of conditions characterized by the elevation of one or more of the following lipid materials: free fatty acids, triglycerides, total cholesterol, and low density lipoprotein cholesterol. Hyperlipidemia may also be associated with decreased high density lipoprotein cholesterol.

During the investigations into, and development of non-addictive morphine based analgesics, typically requiring a combination of agonistic and antagonistic actions at various opiate receptor sites, i.e. $\mu$, $\delta$ and $\kappa$ receptors, a variety of so-called 'pure' antagonists have evolved as by-products, and some of these narcotic antagonists, or anti-opioids, have been shown to have potential in the treatment of a variety of disease conditions.

U.S. Pat. No. 4,272,540 discloses various 14-methoxy substituted 3-hydroxy or 3-methoxy-6-one morphinans, which are variously useful as analgesics, narcotic antagonists, and mixed analgesics and narcotic antagonists.

U.S. Pat. No. 4,451,470 discloses 14-fluoromorphinans which are useful as analgesic, narcotic antagonists and/or anorexigenic agents.

U.S. Pat. No. 4,478,840 discloses 17-cycloalkylmethyl-4-5α-epoxymorphinan-3,14-diol compounds useful for suppression of appetite in mammals.

U.S. Pat. No. 4,511,570 discloses a method of treating senile dementia which comprises periodic oral delivery of a pharmaceutically effective amount of 6-methylen-6-desoxy-N-cyclopropylmethyl-14-hydroxydihydronormorphone.

U.S. Pat. No. 4,619,936 discloses pharmaceutical compositions containing (5α,6α)7,8-didehydro-4,5-epoxy-17-(2-propanyl)-morphinano-3,6-diol for the purpose of appetite reduction.

U.S. Pat. No. 4,857,533 discloses a method of treating a human or animal patient suffering from an autoimmune disease, which comprises the daily administration of the narcotic antagonists nalmefene or naltrexone.

U.S. Pat. No. 4,863,928 discloses a method of treating a human or animal patient suffering from an arthritic disease which comprises the daily administration of the narcotic antagonists nalmefene or naltrexone.

U.S. Pat. No. 4,877,791 discloses a method of treating a human or animal patient suffering from intestinal cystitis which comprises the daily administration of the narcotic antagonists nalmefene or naltrexone.

U.S. Pat. No. 4,880,813 discloses a method of treating patients suffering from allergic rhinitis, which comprises the topical administration to the nasal passages of the narcotic antagonist nalmefene or a salt thereof U.S. Pat. No. 4,882,335 discloses a method useful as an adjunct in the treatment of alcoholism. The method involves having the patient drink alcoholic beverages, while an opiate antagonist blocks the positive reinforcement effects of ethanol in the brain.

U.S. Pat. No. 4,994,466 discloses a method of treating a human or animal patient suffering from multiple sclerosis, which comprises the daily administration to such patient of a pure narcotic antagonist, e.g., nalmefene or naltrexone.

U.S. Pat. No. 5,086,058 discloses a method for treating alcoholism. The method involves having the patient drink alcoholic beverages while nalmefene, an opiate antagonist, blocks the positive reinforcement effects of ethanol in the brain.

U.S. Pat. NO. 5,356,900 discloses a method of treating a human patient suffering from chronic herpes virus infections which comprises administration to such patient of an essentially pure narcotic antagonist exhibiting substantially higher blocking action against $\mu$ opiate receptor sites than against 67 receptor sites.

U.S. Pat. No. 5,468,755 discloses a process for the long term modification and regulation of lipid and carbohydrate metabolism—generally to reduce obesity, insulin resistance, and hyperinsulinemia or hyperglycemia, or both (these are the hallmarks of noninsulin dependent, or type 2 diabetes)—by administration to a patient of a dopamine agonist, e.g. bromocriptine. Administration of the bromocriptine is made over a limited period at a time of day dependent on the normal circadian rhythm of insulin resistant and insulin sensitive humans. The process may be applied to other vertebrate animals.

U.S. Pat. No. 5,626,860 discloses a method for regulating or ameliorating lipid and glucose metabolism, and reducing body fat stores, insulin resistance, hyerinsulinemia, hyperglycemia, hyperlipidemia, elevated blood lipoproteins (such as triglycerides and cholesterol including chylomicrons, VLDL an LDL) and/or increasing in the subject the plasma HDL. The methods comprises administration or timed administration of inhibitors of dopamine beta hydroxylase (DBH), such as fusaric acid and disulfiram. The preferred daily dose of fusaric acid is 5 to 150 mg/kg of body weight. The preferred daily dose of disulfiram is 100 to 500 mg/kg of body weight or 800 to 40,000 mg/day for a subject weighing 80 Kg.

The Merck Index $10^{th}$ Ed., 1983 pp. 491–2 discloses that administration of alcohol after disulfiram therapy causes intense vasodialation of face and neck, tachycardia, and tachypnea followed by nausea, vomiting, pallor and hypotension. Ocassionally convulsions, cardiac arrhythmias, myocardial infarctions may occur. High doses of alcohol, in combination with disulfiram, my cause dizziness, headache, dyspnea unconsciousness, or death.

The Merck Index $10^{th}$ Ed., 1983 p. 883 discloses that metyrosine is an inhibitor of the first and rate-limiting step in catecholamine biosynthesis, hydroxylation of tyrosine to dopa.

The Pharmacological Basis of Therapeutics, Seventh edition (Chapter 18 P.383), 1985 discloses that that the use of disulfuram therapy should be attempted only under careful medical and nursing supervision.

It has been shown that bromocriptine improves glucose tolerance, and decreases insulin values toward normal in patients with prolactin-producing tumors of the pituitary gland. (R. Landgraf et al; *Diabetologia* 13, 1977, pp. 99–104).

Naltrexone, an antiopioid with unequal opioid receptor binding, by an order of magnitude, has been used in an attempt to reduce body weight, but with inconsistent results. (Atkinson et al, *Clin. Pharnacol. Ther.* 10/85:pp 419–422). This report has also raised questions about a potential hepatic toxicity of naltrexone in humans.

Elevated insulin concentrations have been reduced, for a period of a few days, in a select patient population of four women with polycystic ovary syndrome with Acanthosis Nigrians, by administration of Nalmefene (J. R. Givens et al; *J. Clin. Endocr. & Metab.* 64/2, 1987, pp.377–382). Nalmefene, (6-desoxy-6-methylene-naltrexone), is an antiopioid with a structure and relative receptor binding characteristics similar to naltrexone, but of increased potency and without hepatic toxicity. This report covers concentrations of insulin and glucose, the insulin glucose ratio (I/G) as a measure of insulin resistance, as well as growth hormone (GH), luteinizing hormone LH), follicle stimulating hormone (FSH), dehydroepiandrosterone sulfate (DHEAS), cortisol, testosterone and prolactin (PRL) levels during the study. This report does, however, not report any values on blood lipids, i.e. free fatty acids (FFA), triglycerides (TG), and any of the cholesterol fractions.

It has been shown that intracisternal administration of synthetic human β-endorphin in chronically cannulated, conscious, freely moving, adult male rats increased plasma concentrations of epinephrine, norepinephine, and dopamine in a dose related manner (G. R. Van Loon, N. M. Appel and D. Ho; *Endocrinology;* Vol. 109, P. 46, 1981). This is consistent with the hypothesis that endorphins act at unknown sites to increase peripheral catecholamine release. However, the effect of endorphins upon catecholamine binding is not disclosed.

It has been shown that a κ-selective antagonist, nor-binaltorphimine improves the outcome after experimental brain trauma (R. Vink, P. S. Portoghese, and A. I. Faden, *Am. J. Physiol.* 261, 1991). The κ-opioid receptors apparently mediate pathophsysiological changes after traumatic brain injury. The structure of nor-binaltorphimine is shown by the following formula:

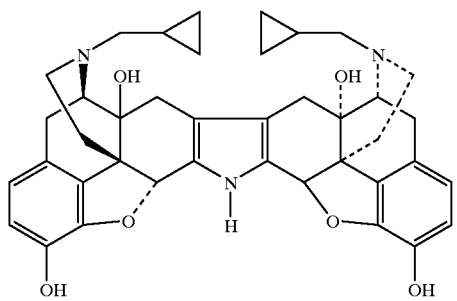

Opiate antagonists, or anti-opioids are molecular structures similar to opiates but without any agonist activity. They have the ability to reduce or prevent the receptor binding of opiate agonists, thus neutralizing their biologic effect. Anti-opioids, or narcotic antagonists, are characterized by their ability to displace narcotic agonists from the respective receptors, and since narcotics, in general, possess several agonist actions, e.g. $\mu$, $\delta$, and $\kappa$, anti-opioids, typically, possess antagonist capabilities for those receptors as well. In general, the antagonist activity, or effectiveness of anti-opioids at the various receptor sites is not equal and may vary significantly, oftentimes by more than an order of magnitude. In such case, e.g. for naltrexone, the $\mu$ receptor binding effectiveness is 12 times higher than its effectiveness to bind to a κ receptor, which will result in a 12-fold increase of agonist displacement at the $\mu$ receptor over the κ receptor. Since the $\mu$ receptor is known to control (amongst others) euphoria, a suppression of this action 12-fold over any action controlled by κ, e.g. various metabolic functions, can, actually result in disphoria, if the antiopioid dosage has to be increased to achieve the desired effect at the κ site.

$IC_{50}$ is defined as the concentration of a compound at which 50% of the standard molecule is displaced from the target receptor. For each receptor there is a prototype ligand. To measure the $IC_{50}$ for given anti-opioid, one measures the concentration of the anti-opioid which will drive 50% of the prototype ligand from the target receptor. For the $\mu$ receptor the prototype ligand is DHM (dihydromorphine). For the $\delta$ receptor, the prototype ligand is DADLE (D-Ala+D-Leu-Enkephalin), and for the κ receptor, the prototype ligand is EKC (ethylketocyclazocine).

SUMMARY OF THE INVENTION

It has been found that the entire CHDRF Syndrome, or individual abnormalities, which make up the syndrome, may be treated as a single entity through the use of a treatment which acts against the root cause of the syndrome rather than against individual symptoms. In contrast to traditional methods of treating the coronary heart disease risk factors separately, at the symptomatic level, the present invention provides a method of treatment of humans suffering from the syndrome of coronary heart disease risk factors (CHDRF Syndrome), or portions of the syndrome, including hyperlipidemia, type 2 diabetes / impaired glucose tolerance, obesity and/or essential hypertension at a central level. The treatment method comprises administering, by a pharmaceutically effective mode, a drug selected from the group consisting of opiate-antagonists or anti-opioids, and drugs which substantially equally reduce the amounts of catecholamines bound at catecholamine receptor sites, particularly the $\alpha_1$, $\alpha_2$, $\beta_1$, and $\beta_2$ epinephine and nor-epinephrine binding sites. The treatment method results in a reduction of the coronary disease risk factors and an amelioration toward normal of fasting blood glucose, HgbAlc, C-peptide, fasting total cholesterol, fasting LDL-cholesterol, fasting HDL-cholesterol, LDL/HDL ratio, fasting triglycerides, fasting free fatty acid concentration, body weight, systolic blood pressure and diastolic blood pressure. For a period of one to four weeks, the drug is administered at a high priming dosage. Thereafter, the drug is administered at a lower maintenance dosage. The maximum priming dosage that may be safely administered depends upon the drug chosen and how large a dose may be given before serious side effects are observed. The priming dosage is about 2.5 times the level of the maintenance dosage. Generally, a priming dose in the range of about 2.5 to about 10 times the maintenance dose of the drug is chosen. Although the drug may be administered in split doses, it has been found that the best results are obtained when the maintenance doses of the drug are given, as a single dose within 3 hours before the patient's normal bedtime.

DETAILED DESCRIPTION OF THE INVENTION

The present invention provides a method for treating the Syndrome of Coronary Heart Disease Risk Factors (CHDRF Syndrome), including hyperlipidemia, type 2 diabetes / impaired glucose tolerance (IGT), obesity and/or essential hypertension. The method also provides a treatment for the individual conditions within the CHDRF Syndrome. Drugs, which are useful in this method, are certain types of anti-opioid drugs and drugs which substantially equally reduces the amounts of catecholamines which are bound to catecholamine binding sites. It is believed that both catecholamines and the endogenous opioids are involved in the complex response to stress. As noted above, there are indications that catecholamines are mediated by endogenous opioids e.g. endorphins and dynorphins in that endorphin administration can lead to increased peripheral catecholamine release.

The treatment method results in a reduction of the coronary disease risk factors and an improvement toward normal values of fasting blood glucose, HgbAlc, C-peptide, fasting total cholesterol, fasting LDL-cholesterol, fasting HDL-cholesterol, LDL/HDL ratio, fasting triglycerides, fasting free fatty acid concentration, body weight, systolic blood pressure, diastolic blood pressure. The method may be used to treat the entire syndrome, or individual portions thereof, which may predominate in the given patient. Specifically, the method may be used to treat elevations in fasting blood glucose, HgbAlc, C-peptide, fasting total cholesterol, LDL-cholesterol, LDL/HDL ratio, fasting triglycerides, fasting free fatty acid concentrations, and elevation in body weight, and to increase fasting HDL-cholesterol In one embodiment the invention involves the control of the CHDRF Syndrome through control of the amounts of catecholamines which are bound at catecholamine binding sites. There are several catecholamine binding sites, particularly the $\alpha_1$, $\alpha_2$, $\beta_1$, and $\beta_2$ epinephrine and nor-epinephrine binding sites, and $D_1$ and $D_2$ dopamine binding sites. I have found that the administration of a drug which substantially equally reduces the amounts of catecholamines bound to catecholamine binding sites, particularity the $\alpha_1$, $\alpha_2$, $\beta_1$, and $\beta_2$ epinephrine and nor-epinephrine binding sites, lowers the levels of free fatty acids, triglycerides, total cholesterol, and low density lipoprotein cholesterol while increasing the level of high density lipoprotein cholesterol. The administration of such a drug also reduces fasting blood glucose concentrations in insulin resistant subjects, and reduces body weight.

Accordingly, in one aspect, this invention relates to a method of treating the CHDRF Syndrome in humans by the administration, in a pharmaceutically acceptable mode, of a drug which substantially equally reduces the amounts of catecholamines bound to catecholamine binding sites, particularly the $\alpha_1$, $\alpha_2$, $\beta_1$, and $\beta_2$ epinephrine and nor-epinephrine binding sites. The method may be used to treat elevation in fasting blood glucose, elevation of HgbAlc, elevation of C-peptide, elevation of fasting total cholesterol, elevation of fasting LDL-cholesterol, a high LDL/HDL ratio, elevation of fasting triglycerides, elevation of fasting free fatty acid concentration, elevation in body weight, and to increase fasting HDL-cholesterol. An appropriate drug may act by interfering with catecholamine synthesis, and thereby reducing the amounts of catecholamines which are available for binding. On the other hand, the drug may act to reduce binding by acting as a catecholamine antagonist at the catecholamine binding sites. Other methods of reducing binding include reduction of catecholamine stores, and enhanced catecholamine clearance.

A single drug which provides equal reduction of amounts of catecholamines bound to catecholamine binding sites, particularly $\alpha_1$, $\alpha_2$, $\beta_1$, and $\beta_2$ epinephine and nor-epinephrine binding sites, is the most desirable treatment method. However, if the reduction of the amounts of catecholamines bound at these binding sites are substantially equal, that is the difference between the various binding reductions is not greater than a factor of three, the method will still work. Accordingly, a drug which substantially equally reduces the amounts of catecholamines bound to catecholamine binding sites is defined as a drug which provides reduction of the amounts of catecholamines bound to catecholamine binding sites, particularly the $\alpha_1$, $\alpha_2$, $\beta_1$, and $\beta_2$ epinephine and nor-epinephrine binding sites, and the degree of reduction of the catecholamine binding for these sites varies by a factor of three or less. The measurement of the degree of reduction of catecholamine binding may be achieved by using radioactive labeled catecholamine agonists or antagonists i.e. selective blockers, and the measurement of the amount of radioactivity incorporated at the respective sites or released into solution. The reduction of amounts of catecholamines bound to catecholamine binding sites particularly the $\alpha_1$, $\alpha_2$, $\beta_1$, and $\beta_2$ epinephine and nor-epinephrine binding sites may be accomplished by a singular agent or by a combination of drugs which, working together, act to control catecholamine synthesis, or act as antagonists to control the binding of catecholamines. Mixtures of drugs may present problems in that rate of absorption, metabolism, and excretion of the individual components may vary. Thus, the mixture that has an ideal balance one hour after the dose is administered may have much poorer balance three hours later. The degree of variability may also differ from patient to patient. Nonetheless, combination drugs are known. It is possible to overcome these problems with the proper selection of catecholamine antagonists or suppressors of catecholamine synthesis. Thus, the drug composition useful in the practice of the present invention may be a single drug or a combination of drugs, which together have the desired effect.

There are a variety of catecholamine agonists and antagonists which act upon various catecholamine receptors including the $\alpha_1$, $\alpha_2$, $\beta_1$, and $\beta_2$ epinephine and nor-epinephrine binding sites. Some of these receptors have effects which counter balance the effects of other receptors. Often blocking one receptor with a suitable antagonist can cause, over time, compensatory changes in the responses of or to other receptors, so that a drug may be effective in the short term but not in the long term. On the other hand, a substantially equal reduction in the amount of catecholamines bound at the various catecholamine binding sites does not trigger such compensatory mechanisms and provides for a treatment modality which has long term effectiveness.

The drugs which reduce the catecholamine binding are first administered, for a period of one to four weeks, at a high priming dosage. Thereafter, the drug is administered at a lower maintenance dosage. The priming dosage is about 2.5 times the level of the maintenance dosage. Generally, a priming dose in the range of about 2.5 to about 10 times the maintenance dose of the drug is chosen. However, the maximum priming dose is limited to the amount that may administered without serious side effects. Although the drug may be administered in split doses, it has been found that the best results are obtained when the maintenance doses of the drug are given, as a single dose within 3 hours before the patient's normal bedtime.

Catecholamines, including epinephrine and norepinephrine may be substantially equally suppressed or reduced by inhibiting the enzyme tyrosine hydroxylase. A drug which accomplishes this inhibition is $\alpha$-methyltyrosine (metyrosine). Metyrosine is a drug which has been used for some time to suppress the synthesis of catecholamines in the in the treatment of pheochromocytoma, a disease characterized by excessive catecholamine release. The typical dose of metyrosine for treatment of pheochromocytoma is 2000 to 4000 mg per day in divided doses. At this high dosage level, patients may suffer Parkinson's disease like symptoms. These symptoms apparently arise because of metyrosine's action in depressing the synthesis of all catecholamises, including dopamine.

In a more limited aspect, this invention relates to a method of treating the Syndrome of Coronary Heart Disease Risk Factors (CHDRF Syndrome), and individual conditions within the CHDRF Syndrome in humans by the administration of metyrosine to such human patients. The drug may be administered by any pharmaceutically acceptable mode. Simple oral administration has been found to be adequate at a daily maintenance dosage in the range of 2 to 10 mg/kg. For a 75 kg adult, this would be a dosage level of 150 to 750 mg per day. Although the drug may be administered in split doses, it has been found that the best results are obtained when the maintenance dose of the drug is given, as a single dose within 3 hours before the patient's normal bedtime. The priming dose could be as large as about 2000 mg per day since this dose is generally tolerated, although as noted above there may be occasional side effects at such levels. The preferred priming dose is about 2.5 times the maintenance dose or 5 to 40 mg/kg. For a 75 kg adult, the priming dose would be in the range of about 375 mg to about 2000 mg per day. The higher priming doses should be administered as divided doses. At the maintenance level, Parkinson's disease like symptoms would not generally be expected.

In order to further reduce the risk such Parkinson's disease like side effects, they can be avoided by the co-administration of dopamine agonist such as 2-bromo-α-ergocryptine (bromocriptine); 6-methyl-8β-carbobenzyloxy-aminoethyl-10α-ergoline; 1,6-dimethyl-8β-carbobenzyloxy-aminoethyl-10α-ergoline; 8-acylamino-ergolines such as 6-methyl-8α-(N-acyl)amino-9-ergolene; 6-methyl-8α-(N-phenylacetyl)-amino-9-ergolene; ergocornine; 9,10-dihydroergocornine; and D-2-halo-6-alkyl-8substituted ergolines. Bromocryptine is the favored dopamine agonist for use in preventing the Parkinson's disease like symptoms which may accompany the use of metyrosine.

Bromocryptine is dopamine agonist and thus acts like dopamine within the body. On the other hand, metyrosine is a catecholamine suppressor, and as such, lowers the level of catecholamines, including dopamine, in the body. Surprisingly, although bromocryptin and metyrosine seem to have opposite actions, bromocryptin does not interfere with the action of metyrosine in alleviating the CHDRF Syndrome.

EXAMPLE I

A 54 year old male insulin resistant subject was given 250 mg metyrosine twice daily. After 8 weeks of this treatment regimen, his fasting blood glucose level (BGL) had decreased by 10% from 121 to 110 mg/dl, insulin by 32% from 19 to 13 µU/ml, free fatty acids (FFA) by 23% from 742 to 575 µE/L, triglycerides (TG) by 31% from 208 to 144 mg/dl, total cholesterol (TCH) by 30% from 299 to 209 mg/dl, LDL by 24% from 176 to 134 mg/dl, and HDL by 34% from 41 to 27 mg/dl, with a resulting LDL/HDL ratio initially increasing from 4.3 to 5.0, both values being outside the normal range.

After another 6 weeks of the treatment regimen (a total of 14 weeks), LDL decreased further from 134 to 119 mg/dl, resulting in a total reduction of 32% from the beginning of the study, and HDL increased to 39 mg/dl resulting in an LDL/HDL ratio of 3.1, now well within the normal range of 1.0–4.0. There was a slight decrease in body weight at week 8. Four (4) weeks following the discontinuation of the treatment regimen, all values returned essentially to their pre-study levels (Table I).

TABLE I

| | Glucose mg/dl | Insulin µU/ml | FFA µE/ml | TG mg/dl | Chol. Tot mg/dl | LDL mg/dl | HDL mg/dl | LDL/HDL |
|---|---|---|---|---|---|---|---|---|
| INITIAL LEVELS | 121 | 19 | 742 | 208 | 299 | 176 | 41 | 4.3 |
| 8 WEEKS | 110 | 13 | 575 | 144 | 209 | 134 | 27 | 5.0 |
| 14 WEEKS | — | — | — | — | — | 119 | 39 | 3.1 |
| 4 WEEKS AFTER DISC. | 122 | 15 | 747 | 211 | 254 | 189 | 37 | 5.1 |

In another embodiment, the invention relates to the treatment of the coronary heart disease risk factor syndrome (CHDRFS), by the administration, of drugs which act as narcotic antagonists, also referred to as opiate antagonists, or anti-opioids. The term opioid and opiate are equivalent, and are used interchangeably herein. These anti-opioids interact with the natural opiate receptors and thereby block the receptors from interacting with opiate drugs. This effect of blocking the action of opiate drugs extends not only to blocking the traditional opium alkaloid drugs, but also to blocking the action of the endogenous beta-endorphins, dynorphins and enkephalins produced within the human body.

In one embodiment, the CHDRFS may be treated by the administration of a single drug or, mixtures of drugs, with purely opiate antagonistic effects, such as naloxone, naltrexone, nalmefene or 17-cyclopropylmethyl-3-hydroxy-14-methoxy-8βmethylmorphinan-6-one hydrochloride (CHMMO) by a pharmaceutically acceptable mode. In another embodiment, the CHDRFS may be treated by the administration of a mixture of drugs, with net opiate antagonistic effects, by a pharmaceutically acceptable mode. Such a mixture could include small quantities of opiate agonists which would serve to modify the balance of the antagonist properties of the anti-opiods. The amount of opioid agonists is such that the net effect of the mixture is antagonistic to all opioid receptors. Such a mixture would act as an anti-opioid and it would not be addictive, nor would its use lead to tolerance.

There are several types of opiate receptor sites and the opiate antagonists do not, generally, have an equipotent effect on all the different receptor sites. In evaluating opiate antagonists for use in the treatment of any or all of the CHDRF'S, their interaction with the $\mu$, $\delta$, and $\kappa$ opiate receptors is most important. Opiate antagonists, such as naloxone and naltrexone, which exert their greatest effect upon the $\mu$ receptors, may be used to treat the CHDRFS, but may have undesirable CNS side effects due to their differing levels of effectiveness against the $\mu$, $\delta$, and $\kappa$ opioid receptors. Opioid antagonists which have approximately equal effects on the $\mu$, $\delta$, and $\kappa$ receptors are useful for the treatment of CHDRFS in humans. If such anti-opioids are used, they should have $IC_{50}$'s for the $\mu$, $\delta$, $\kappa$ opiate receptors be within a factor of 10 of each other, and, if possible, the $IC_{50}$'s should differ by a factor of less than three. However, it has been discovered that inhibition of the $\kappa$ opiate receptor is important in determining the effect of an anti opioid on the CHDRFS. It is preferred that the anti-opioids have an effect upon the κ opiate receptor as strong as or stronger than effect upon the μ, and δ opiate receptors. Since a strong inhibitory effect means that the anti-opioid is effective at low concentrations, it is desirable that the anti-opioids have a lower $IC_{50}$ for the κ opiate receptor than for the μ, and δ opiate receptors.

The relationship between the $IC_{50}$ levels for the μ, δ, κ opiate receptors may also be expressed in terms of a ratio. For example, if the $IC_{50}$ level for the μ, opiate receptor is within a factor of 3 of the $IC_{50}$ level for the δ opiate receptor then the ratio of the $IC_{50}$ level for the μ, opiate receptor to the $IC_{50}$ level for the δ opiate receptor may be expressed in the following manner: $\frac{1}{3}<(IC_{50} \delta/IC_{50} \mu)<3$. The preferred anti-opioids or antiopioid combinations for use in the treatment of CHDRFC have a ratio of $IC_{50}$ for the κ opiate receptor to the $IC_{50}$ for the μ or δ receptors of 10 or less and most preferably 3 or less. These preferred compositions may be expressed as a ratio of $IC_{50}$ values: $\{(IC_{50} \kappa/ IC_{50} \mu)<10\}$, and $\{(IC_{50} \kappa/ IC_{50} \delta)<10\}$; and the most preferred compositions have $IC_{50}$ values: $\{(IC_{50} \kappa/ IC_{50} \mu)<3\}$, and $\{(IC_{50} \kappa/ IC_{50} \delta)<3\}$. A κ selective opioid antagonist such as nor-binaltorphimine is useful in the treatment of any or all of the conditions which make up the CHDRFS. It may be used alone, or in combination with other anti-opioid drugs. When used as part of a combination drug, it serves to add further inhibition of the κ opioid receptors to the properties of the combination.

The anti-opioid drugs are first administered, for a period of one to four weeks, at a high priming dosage. Thereafter, the drug is administered at a lower maintenance dosage. The priming dosage is at about 2.5 times the level of the maintenance dosage. Generally, a priming dose in the range of about 2.5 to about 10 times the maintenance dose of the drug is chosen. However, the maximum priming dose is limited to the amount that may administered without serious side effects. Although the drug may be administered in split doses, it has been found that the best results are obtained when the maintenance doses of the drug are given, as a single dose within 3 hours before the patient's normal bedtime.

EXAMPLE II

A 56 year old insulin resistant male subject was given 17-cyclopropylmethyl-3-hydroxy-14-methoxy-8β-methylmorphinan-6-one hydrochloride (CEMMO), a pure opioid antagonist, in two daily doses of 18 mg each for the duration of one week, followed by 9 mg b.i.d. for another 4 weeks. Blood glucose dropped by 15% from 111 to 95 mg/dl during the first week and remained essentially at the same level for the duration of the study and, by the end of the study, after 5 weeks, insulin level had fallen by about 50% from 14 to 6 μU/ml, FFA by 23% from 754 to 580 μE/L, TG by 42% from 229 to 133 mg/dl, Total Cholesterol by 21% from 234 to 185 mg/dl, LDL by 7% from 156 to 145 mg/dl, and HDL increased by 20% from 30 to 36 mg/dl, improving the LDL/HDL Ratio by 23% from 5.2 to 4.0 over the study duration of 5 weeks. There was also a slight weight loss at the end of the study (Table II).

TABLE II

| | Gluc. mg/dl | Insulin μU/ml | FFA mM/L | TG mg/dl | CH. T mg/dl | LDL mg/dl | HDL mg/dl | LDL/ HDL | Alk.-Phos | AST U/L | ALT U/L | LD U/L |
|---|---|---|---|---|---|---|---|---|---|---|---|---|
| day 1 | 111 | 14 | 0.75 | 229 | 234 | 156 | 30 | 5.2 | 145 | 23 | 29 | 162 |
| day 41 | 95 | 6 | 0.58 | 133 | 185 | 145 | 36 | 4.0 | 126 | 16 | 20 | 117 |

EXAMPLE III

A 69 year old male subject with Impaired Glucose Tolerance and borderline Type 2 Diabetes was given Nalmefene, a pure opioid antagonist meeting the anti-opioid receptor binding characteristics of δ,κ,μ $IC_{50}$ being within a factor of 10, and/or κ $IC_{50}/\mu,\delta IC_{50}<10$. The results achieved with 2 daily doses of 0.5 mg each are tabulated in Table III. This Table III also illustrates, for comparative purposes, the results achieved with CHMMO, as tabulated in Table II. CHMMO meets the anti-opioid receptor binding characteristics of δ,κ,μ $IC_{50}$ being within a factor of 3, and/or $\{(IC_{50} \kappa/ IC_{50} \mu)<3\}$, and $\{(IC_{50} \kappa/ IC_{50} \delta)<3\}$.

TABLE III

| | | Nalmefene. 0.5 mg b.i.d. | | | CHMMO 9.0 mg b.i.d. | | |
|---|---|---|---|---|---|---|---|
| | Normal Values | Day 1 | Day 141 | Δ% | Day 1 | Day 41 | Δ% |
| Enzymes | | | | | | | |
| Alk-phos | 35–130 U/L | 70 | 72 | 3 | 145 | 126 | 6 |
| GG-transp | 0–85 U/L | 56 | 32 | 43 | | | |
| AST | 0–50 U/L | 31 | 16 | 48 | 23 | 16 | 30 |
| ALT | 0–165 U/L | 72 | 42 | 42 | 29 | 20 | 31 |
| LD | 90–200 U/L | 125 | 120 | 4 | 162 | 117 | 27 |
| Substrates | | | | | | | |
| Glucose | 70–110 mg/dl | 138 | 120 | 13 | 111 | 95 | 14 |
| HgbA1c | 4.3–6.1% | 6.0 | 5.4 | 10 | | | |
| Insulin | 5–35 μU/ml | 27 | 16 | 43 | 14 | 6 | 50 |
| C-Peptide | 0.9–3.9 ng/ml | 4.7 | 2.9 | 38 | | | |

TABLE III-continued

|  | Normal Values | Nalmefene. 0.5 mg b.i.d. | | | CHMMO 9.0 mg b.i.d. | | |
| --- | --- | --- | --- | --- | --- | --- | --- |
|  |  | Day 1 | Day 141 | Δ% | Day 1 | Day 41 | Δ% |
| Lipids |  |  |  |  |  |  |  |
| Chol. Total | <200 mg/dl desirable 200–239 borderline | 247 | 193 | 22 | 234 | 185 | 21 |
| LDL-C. | <130 mg/dl desirable | 140 | 118 | 16 | 156 | 145 | 7 |
| HDL-C. | 35–70 mg/dl | 37 | 40 | 8 | 30 | 36 | 16 |
| LDL/HDL |  | 3.78 | 2.95 | 22 | 5.2 | 4.03 | 22 |
| TG | 10–190 mg/dl | 270 | 175 | 35 | 229 | 133 | 42 |
| FFA | 0.1–0.6 mM/L | 0.68 | 0.41 | 40 | 0.75 | 0.58 | 22.7 |
| Weight | 79 kg; 179 cm height | 86 | 79 | 8 | 82 | 80 | 4.5 |
| Blood Pressure |  | 136/ 100 | 128/ 83 | 8 pts 17 pts |  |  |  |

Alk-phos = alkaline phosphatase
GG-trans = Gamma glutamyltransferase
AST = Aspartate aminotransferase
ALT = Alanine aminotransferase
HgbA1c =0 Hemoglobin A1c
Chol.-Total = Total cholesterol
LDL-C = Low density lipo-protein cholesterol
HDL-C = High density lipo-protein cholesterol
TG = Triglycerides
FFA = Free fatty acids The treatment method resulted in improvements of clinical measurements relating to the glucose metabolism portion of the CHDRFS, in particular, a 13% reduction in fasting blood glucose, a 10% reduction in HgbAlc, and a 38% reduction in fasting C-Peptide concentration.

The treatment method resulted in improvements of clinical measurements relating to the lipid metabolism portion of the CHDRFS, in particular, a 22% reduction in fasting total cholesterol, a 16% reduction in fasting LDL-Cholesterol, an 8% increase in fasting HDL-Cholesterol, a 22% improvement in the LDL/IDL ratio, a 35% reduction in fasting triglyceride (TG) levels, and a 40% reduction in fasting free fatty acid (FFA) concentration.

The treatment method resulted in improvements of clinical measurements relating to the essential hypertension and obesity lipid portion of the CHDRFS, in particular, a reduction of weight of 8%, down to normal weight, and a reduction in the blood pressure of 8 points systolic and 17 points diastolic.

The results obtained with the anti-opioids in EXAMPLES II and HI are similar to those achieved with metyrosine in EXAMPLE I. These examples illustrate an important feature of the invention, that is, the treatment of the entire CHDRFS as a single condition rather than symptomatic treatment of specific portions of the syndrome such as hyperlipidemia, essential hypertension, type 2 diabetes / impaired glucose tolerance, and/or obesity. The improvement in the liver enzymes shown in EXAMPLE III provides an indication that this treatment method does not present the risk of negative hepatic side-effects.

The receptor binding on $\mu$, $\delta$, and $\kappa$ opioid receptors for Naloxone, Naltrexone, CHMMO, and Nalmefene are:

|  | $\mu$ IC$_{50}$ | $\delta$ IC$_{50}$ | $\kappa$ IC$_{50}$ |
| --- | --- | --- | --- |
| Naloxone | $3.8 \times 10^{-9}$M | $2.7 \times 10^{-8}$M | $6.0 \times 10^{-8}$M |
| Naltrexone | $1.0 \times 10^{-9}$M | $1.0 \times 10^{-8}$M | $1.2 \times 10^{-8}$M |
| CHMMO | $5.0 \times 10^{-10}$M | $8.0 \times 10^{-10}$M | $9.5 \times 10^{-10}$M |
| Nalmefene | $1.0 \times 10^{-9}$M | $0.6 \times 10^{-8}$M | $0.5 \times 10^{-8}$M |

Although it is preferred to find the proper IC$_{50}$ level's for the $\mu$, $\delta$, and $\kappa$ receptors opiate receptors within a single molecule one should not preclude the possibility of the use of a mixture of opiate antagonists. Mixtures of molecules may present problems in that the rate of absorption, metabolism, and excretion of the individual components may vary. Thus, the mixture that has an ideal balance one hour after the dose is administered, may have much poorer balance three hours later. The degree of variability may also differ from patient to patient. Nonetheless, combination drugs are known. It is possible to overcome these problems with the proper selection of opiate antagonists and produce, for example, a composition with opiate antagonist properties such that the combined IC$_{50}$ levels for the $\mu$, $\delta$, and $\kappa$ opiate receptors have a ratio of IC$_{50}$ for the $\kappa$ opiate receptor to the IC$_{50}$ for the $\mu$ or $\delta$ receptors of 10 or less and most preferably 3 or less. Some anti-opioids are more effective in binding to $\mu$ and $\delta$ receptors than to $\kappa$ receptors. The effectiveness of the combination against to $\kappa$ receptors may be enhanced by adding a $\kappa$-selective opiate antagonist such as nor-binaltorphimine to the combination, in order to achieve a combination having the desired properties. The same technique may be applied to enhance the effectiveness of a combination in binding to the $\mu$ and $\delta$ receptors. For example, an anti-opioid which is more effective in binding to $\kappa$ and $\mu$ receptors than to $\delta$ receptors, the effectiveness of the combination against to $\delta$ receptors may be enhanced by adding a $\delta$-selective opiate antagonist to the combination, in order to achieve a combination having the desired properties. Similarly, adding a $\mu$-selective opiate antagonist to the combination, would enhance the effectiveness of the combination in binding to $\mu$ receptors.

Another method for achieving the desired balance of antagonist activity is to add a small quantity of an opioid agonist to an antagonist which has unbalanced inhibition of the various receptors. The agonist drug competes with the antagonist for the particular receptor, and diminishes, but does not totally remove the antagonist properties of the anti-opioid. For example, nalmefene has a IC$_{50}$ $\kappa$/ IC$_{50}$ $\mu$ ratio of 5. If nalmefene is combined with a small amount of a drug which has an agonist effect on only the ft receptor, such as dihydromorphine (DHM), the net result is that the combination drug has a lower $IC_{50}$ κ/ $IC_{50}$ μ ratio than pure nalmefene. Since the effect of DHM on the μ receptor does not effect the action of nalmefene on the κ and δ receptors, the addition of DHM to nalmefene brings the δ $IC_{50}$, κ $IC_{50}$, and μ $IC_{50}$ closer to each other.

The drug composition comprises a composition with opiate antagonist properties useable in the present invention may be single substances with purely opioid antagonist activity. The drug compositions may also be a combination of such anti-opioid activity. The drug composition may also include an opioid agonist as long as the combination has a net opioid antagonist effect.

A correlation between the structure of the opiate antagonist and the relative strength of receptor binding has not been established. However, it is clear that any opiate antagonist or antagonist combination which has the proper $IC_{50}$ level's for the μ, δ, and κ opiate receptors may be used in an embodiment of present invention in order to achieve the expected beneficial results in the treatment of CHDRFS.

The anti-opioid drugs of this class have a very low level of negative side effects, if any. Even fewer are expected when these drugs are used in treating the CHDRFS because in this therapy the maintenance doses are very small. For example, the effective daily maintenance dosage range for Nalmefene is between 2 μg/kg and 200 μg/kg body weight. The preferred dosage range is between 4 μg/kg and 40 μg/kg body weight. For other anti-opioid drugs, the effective level may vary depending upon factors such as the $IC_{50}$ levels of the drug, the absorption rate, bio-availability, excretion rate and the rate of metabolism of the drug. Although the drug may be administered in split doses, it has been found that the best results are obtained when the maintenance doses of the drug are given, as a single dose within 3 hours before the patient's normal bedtime.

The drugs administered according to the present invention may be administered in any pharmaceutically effective mode. Pharmaceutically effective modes include applications of the drug as a solution in an innocuous solvent, as an emulsion, suspension or dispersion in suitable carriers, application of the drug in the form of pills or capsules together with solid carriers, and other such methods well known in the art. The formulations of this invention may include pharmaceutically acceptable excipients such as stabilizers, anti-oxidants, binders, coloring agents, emulsifiers, and other such excipients well known in the art.

What is claimed is:

1. A method of treatment of humans suffering from one or more conditions included within the CHDRF Syndrome, comprising the steps of: 1) administering, by a pharmaceutically effective mode, a priming dose of a drug composition comprising a drug substance selected from the group consisting of opiate antagonists, and drugs which substantially equally reduce the amounts of catecholamines bound to catecholamine binding sites for a period of about one to four weeks, and 2) administering a maintenance dose of said selected drug at a dosage level of between 1/10 to 1/2.5 times the priming dose.

2. A method according to claim 1 wherein the maintenance dose is administered as a single dose within 3 hours before the patients normal bedtime.

3. A method according to claim 1 wherein the drug composition comprises a drug composition which substantially equally reduce the amounts of catecholamines bound to catecholamine binding sites.

4. A method according to claim 3 wherein the drug composition further contains a dopamine agonist.

5. A method of treating humans suffering from the CHDRF Syndrome, according to claim 3 wherein the drug composition comprises α-methyltyrosine.

6. A method of treating humans suffering from the CHDRF Syndrome according to claim 1 wherein the drug composition further comprises an opiate antagonist.

7. A method according to claim 6 wherein the drug composition comprises a single drug.

8. A method according to claim 6 wherein the drug composition comprises nalmefene.

9. A method according to claim 6 wherein the drug composition comprises 17-cyclopropylmethyl-3-hydroxy-14-methoxy-8β-methylmorphinan-6-one hydrochloride (CHMMO).

10. A method according to claim 6 wherein the drug composition comprises a combination of drugs each of which has purely opioid antagonist activity.

11. A method according to claim 6 wherein the drug composition comprises a composition containing one or more drugs which have opioid agonist activity.

12. A method of treating humans suffering from the CHDRF Syndrome according to claim 6 in which the drug composition with opiate antagonist properties has $IC_{50}$ levels for the μ, δ, and κ opiate receptors equal within a factor of 10.

13. A method of treating humans suffering from the CHDRF Syndrome according to claim 6 in which the drug composition with opiate antagonist properties has $IC_{50}$ levels for the μ, δ, and κ opiate receptors equal within a factor of three.

14. A method of treating humans suffering from the CHDRF Syndrome according to claim 6 in which the drug composition with opiate antagonist properties has $IC_{50}$ levels for the μ, δ, and κ opiate receptors have ratios such that:

$$\{(IC_{50} \kappa/IC_{50} \mu)<10\}, \text{ and } \{(IC_{50} \kappa/ IC_{50} \delta)<10\}.$$

15. A method of treating humans suffering from the CHDRF Syndrome according to claim 6 in which the drug composition with opiate antagonist properties has $IC_{50}$ levels for the μ, δ, and κ opiate receptors such that: $\{(IC_{50}\kappa/IC_{50} \mu)<3\}$, and $\{(IC_{50} \kappa/ IC_{50} \delta)<3\}$.

16. A method according to claim 6 wherein the drug composition comprises a κ-selective opioid antagonist.

17. A method according to claim 6 wherein the drug composition comprises nor-binaltorphimine.

18. A method according to claim 1 wherein the condition included within the CHDRF Syndrome, is hyperlipidemia.

19. A method according to claim 1 wherein the condition included within the CHDRF Syndrome, is type 2 diabetes.

20. A method according to claim 1 wherein the condition included within the CHDRF Syndrome, is impaired glucose tolerance (IGT).

21. A method according to claim 1 wherein the condition included within the CHDRF Syndrome, is obesity.

22. A method according to claim 1 wherein the condition included within the CHDRF Syndrome, is essential hypertension.

* * * * *